US012115086B2

(12) United States Patent
Arcos et al.

(10) Patent No.: US 12,115,086 B2
(45) Date of Patent: Oct. 15, 2024

(54) ASSEMBLIES FOR DETERMINING HEIGHT AND ANGLE OF AN INTERVERTEBRAL DEVICE

(71) Applicant: AXIS SPINE TECHNOLOGIES LTD, St. Albans (GB)

(72) Inventors: Jonathan Arcos, St. Albans (GB); Christopher Reah, St. Albans (GB); Charles Barfield, Hernando, MS (US); Michael Sherman, Memphis, TN (US)

(73) Assignee: AXIS SPINE TECHNOLOGIES LTD, St. Albans (GB)

( * ) Notice: Subject to any disclaimer, the term of this patent is extended or adjusted under 35 U.S.C. 154(b) by 450 days.

(21) Appl. No.: 17/629,351

(22) PCT Filed: Jul. 24, 2020

(86) PCT No.: PCT/GB2020/051795
§ 371 (c)(1),
(2) Date: Jan. 21, 2022

(87) PCT Pub. No.: WO2021/014176
PCT Pub. Date: Jan. 28, 2021

(65) Prior Publication Data
US 2022/0249255 A1 Aug. 11, 2022

(30) Foreign Application Priority Data
Jul. 25, 2019 (GB) .................................... 1910668

(51) Int. Cl.
*A61F 2/46* (2006.01)
*A61B 17/02* (2006.01)
(Continued)

(52) U.S. Cl.
CPC .......... *A61F 2/4657* (2013.01); *A61B 17/025* (2013.01); *A61F 2/447* (2013.01);
(Continued)

(58) Field of Classification Search
CPC ...... A61F 2/4657; A61F 2/447; A61F 2/4603; A61F 2/4611; A61F 2002/30266;
(Continued)

(56) References Cited

U.S. PATENT DOCUMENTS 6,045,579 A 4/2000 Hochshuler et al.
6,102,950 A 8/2000 Vaccaro
(Continued)

FOREIGN PATENT DOCUMENTS

DE 102012023042 11/2013
EP 2719360 4/2014
(Continued)

OTHER PUBLICATIONS

Product Brochure "InFix Anterior Lumbar Device—Surgical Technique Guide", Zimmer Biomet, 2018, pp. 1-28. Copyright 2018.
(Continued)

*Primary Examiner* — Jessica Weiss
(74) *Attorney, Agent, or Firm* — LIU & LIU

(57) ABSTRACT

An assembly for determining height and angle of an intervertebral device to be implanted in an intervertebral space. The assembly comprises a sizing instrument (12) comprising a support (18) attached to first and second arms (20), (22) which extend in generally a same direction from the support. The assembly also comprises superior and inferior endplates (14), (16) of the intervertebral device to be implanted. One of the superior and inferior endplates (14), (16) engages with a distal end of the first arm (20) and the other of the superior and inferior endplates (14), (16) engages with a distal end of the second arm (22), the superior and inferior endplates opposing each other when they are engaged with their respective arms. The distal end of the second arm (22) performs first and second forms of movement relative to the distal end of the first arm (20), the
(Continued)

first and second forms of movement being independent of each other, the distal end of the second arm moving along different respective paths in the first and second forms of movement, the first form of movement changing separation between the superior and inferior endplates (14), (16), and the second form of movement changing an angle between the superior and inferior endplates (14), (16). The support (18) comprises a user control which is mechanically coupled to at least the second arm (22) of the first and second arms to provide upon user operation of the user control each of the first and second forms of movement of the distal end of the second arm.

18 Claims, 7 Drawing Sheets

(51) Int. Cl.
  *A61F 2/44* (2006.01)
  *A61F 2/30* (2006.01)
(52) U.S. Cl.
  CPC .......... *A61F 2/4603* (2013.01); *A61F 2/4611* (2013.01); *A61B 2017/0256* (2013.01); *A61F 2002/30266* (2013.01); *A61F 2002/30538* (2013.01); *A61F 2002/30556* (2013.01); *A61F 2002/4622* (2013.01); *A61F 2002/4628* (2013.01); *A61F 2002/4658* (2013.01)
(58) Field of Classification Search
  CPC .. A61F 2002/30538; A61F 2002/30556; A61F 2002/4622; A61F 2002/4628; A61F 2002/4658; A61B 17/025; A61B 2017/0256
  USPC .......................................................... 606/102
  See application file for complete search history.

(56) References Cited

U.S. PATENT DOCUMENTS

| | | | |
|---|---|---|---|
| 6,113,637 | A | 9/2000 | Gill et al. |
| 6,582,451 | B1* | 6/2003 | Marucci ................. A61B 17/29 606/207 |
| 7,588,573 | B2* | 9/2009 | Berry ........................ A61F 2/44 606/53 |
| 8,241,294 | B2* | 8/2012 | Sommerich ............... A61F 2/44 606/86 A |
| 8,308,804 | B2 | 11/2012 | Krueger |
| 8,388,686 | B2 | 3/2013 | Aebi et al. |
| 9,402,739 | B2 | 8/2016 | Weiman et al. |
| 9,526,628 | B2 | 12/2016 | Krueger |
| 9,585,765 | B2 | 3/2017 | Niemiec et al. |
| 9,801,734 | B1 | 10/2017 | Stein et al. |
| 10,130,493 | B2* | 11/2018 | Moskowitz ........... A61F 2/4611 |
| 10,159,583 | B2* | 12/2018 | Dietzel ................. A61F 2/4657 |
| 2002/0143399 | A1 | 10/2002 | Sutcliffe |
| 2003/0187506 | A1 | 10/2003 | Ross et al. |
| 2003/0229355 | A1* | 12/2003 | Keller ................... A61F 2/4611 606/247 |
| 2004/0254644 | A1 | 12/2004 | Taylor |
| 2005/0021042 | A1* | 1/2005 | Marnay ................. A61F 2/4611 606/99 |
| 2005/0182416 | A1* | 8/2005 | Lim ................... A61B 17/8858 606/90 |
| 2006/0015183 | A1 | 1/2006 | Gilbert et al. |
| 2007/0016221 | A1 | 1/2007 | Beyersdorff et al. |
| 2007/0233152 | A1 | 10/2007 | Stad et al. |
| 2007/0270957 | A1 | 11/2007 | Heinz |
| 2007/0276498 | A1 | 11/2007 | Aebi et al. |
| 2008/0082169 | A1 | 4/2008 | Gittings et al. |
| 2008/0082173 | A1 | 4/2008 | Delurio et al. |
| 2008/0294260 | A1 | 11/2008 | Gray |
| 2011/0153020 | A1 | 6/2011 | Abdelgany et al. |
| 2011/0184522 | A1 | 7/2011 | Melkent et al. |
| 2013/0006357 | A1 | 1/2013 | Krueger |
| 2013/0085573 | A1 | 4/2013 | Lemoine et al. |
| 2013/0103153 | A1 | 4/2013 | Blackwell et al. |
| 2013/0158667 | A1 | 6/2013 | Tabor et al. |
| 2015/0164494 | A1 | 6/2015 | Glazer |
| 2015/0320568 | A1 | 11/2015 | Ameil et al. |
| 2016/0116396 | A1 | 4/2016 | Hunt et al. |
| 2016/0166396 | A1 | 6/2016 | McClintock |
| 2016/0213483 | A1 | 7/2016 | To et al. |
| 2016/0287403 | A1 | 10/2016 | Suddaby et al. |
| 2017/0143506 | A1 | 5/2017 | Suddaby et al. |
| 2017/0196698 | A1 | 7/2017 | Kim |
| 2017/0239063 | A1 | 8/2017 | Predick |
| 2018/0000606 | A1 | 1/2018 | Hessler et al. |
| 2018/0036141 | A1 | 2/2018 | O'Neil et al. |
| 2018/0098860 | A1 | 4/2018 | To et al. |
| 2018/0256357 | A1 | 9/2018 | To et al. |
| 2022/0015919 | A1 | 1/2022 | Reah et al. |
| 2022/0015920 | A1 | 1/2022 | Reah et al. |
| 2022/0015921 | A1 | 1/2022 | Reah et al. |

FOREIGN PATENT DOCUMENTS

| | | |
|---|---|---|
| WO | 00/19911 | 4/2000 |
| WO | 2004/089224 | 10/2004 |
| WO | 2013184946 | 12/2013 |
| WO | 2014093136 | 6/2014 |
| WO | 2020165586 | 8/2020 |
| WO | 2021014173 | 1/2021 |

OTHER PUBLICATIONS

Product Brochure "SYNFIX Evolution Secured Spacer System", DePuy Synthes, 2016, pp. 1-78. Copyright 2016.
International Search Report of Counterpart PCT International Application No. PCT/GB2020/051789.
International Search Report of Counterpart PCT International Application No. PCT/GB2020/051795.
Product Brochure "Aero-LL Lateral Lumbar Interbody and Fixation System", Stryker Spine, 2016, pp. 1-52.
International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.
International Search Report of Counterpart PCT International Application No. PCT/GB2020/050328.

* cited by examiner

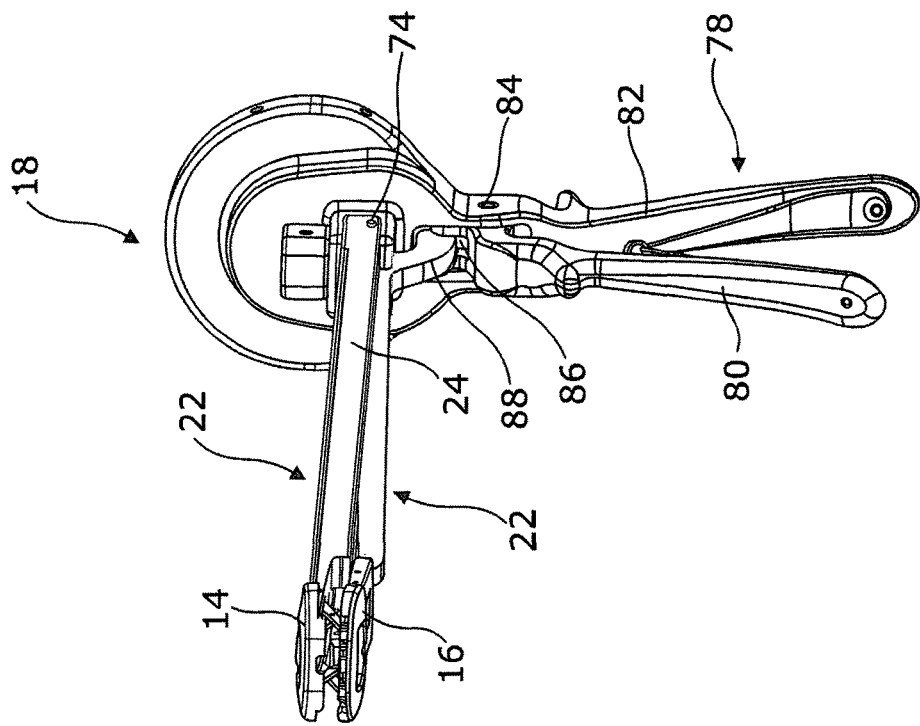
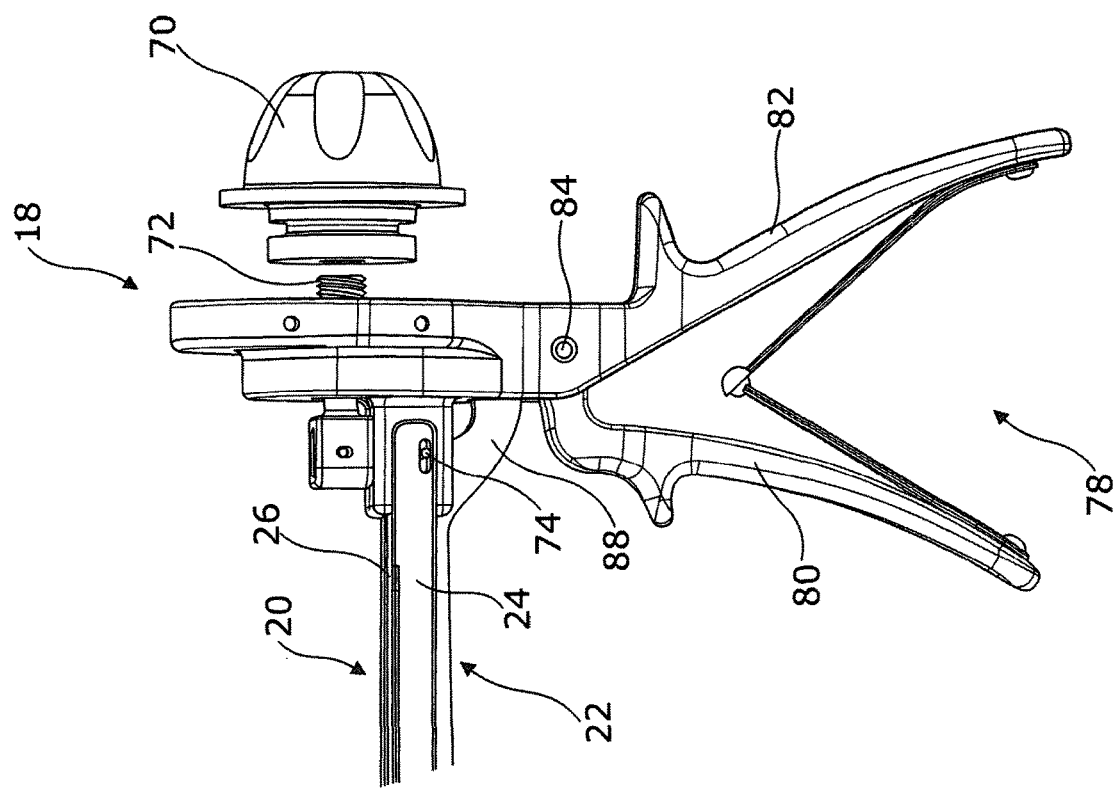
Figure 3A
Figure 3B

ASSEMBLIES FOR DETERMINING HEIGHT AND ANGLE OF AN INTERVERTEBRAL DEVICE

FIELD OF THE INVENTION

The present invention relates to assemblies for and methods of determining height and lordotic angle of an intervertebral device to be implanted in an intervertebral space.

BACKGROUND ART

Adjacent vertebrae in the spinal column are coupled to each other by a number of ligaments and the intervertebral disc. These anatomic structures hold the adjacent vertebrae together while allowing motion. Among these structures, the intervertebral disc functions as a cushion between the vertebrae whilst allowing for relative movement of the vertebrae. Problems with intervertebral discs arise from one or more of a range of diseases and conditions. A surgical procedure, such as an anterior spinal fusion, may be used to address such problems. The goals of anterior spinal fusion include decompressing any surrounding neural structures, re-establishing anatomic spinal alignment and stabilizing the motion segment by having one vertebral body fuse, or heal, to the adjacent vertebral body. A typical spinal fusion procedure involves partial or full removal of a problematic intervertebral disc and installation of an intervertebral device in the place of the partially or fully removed intervertebral disc in order to maintain the disc space height and alignment and facilitate the fusion of one vertebra to the next.

Considering a typical anterior spinal fusion procedure further, after removal of the problematic intervertebral disc and cleaning of the intervertebral space, footprint trials are often carried out to determine the appropriate size required of an intervertebral device to be installed in the intervertebral space. A known approach to determining the appropriate size of intervertebral implant involves use of one or more footprint trial tools. Each footprint trial tool is typically an elongate member with a handle at one end and a trial plate at the other end. A range of footprint trial tools having trial plates of different footprint is typically provided. For example, the trial plates of different footprint may consist of a small footprint trial plate, a medium footprint trial plate and a large footprint trial plate with each corresponding to a group of different size implants. When determining the appropriate size of intervertebral implant, the trial plates of different footprint trial tools are inserted into the intervertebral space until the appropriate footprint is determined. Thereafter, intervertebral device height and angle trials are carried out.

According to a first known anterior approach to intervertebral device height and angle trials, a unitary trial intervertebral device of known height and lordotic angle is mounted on the end of an intervertebral device trial tool. The intervertebral device trial tool is held by a handle at the end of the intervertebral device trial tool opposite the end at which the trial intervertebral device is mounted and the trial intervertebral device is inserted into the intervertebral space. If the trial intervertebral device is found to be of incorrect height and/or angle after visual inspection and perhaps also inspection by way of fluoroscopy, the trial intervertebral device on the intervertebral device trial tool is changed for a second trial intervertebral device of different and more appropriate height and/or angle. The second trial intervertebral device is then inserted into the intervertebral space to determine appropriateness of its height and lordotic angle. This process is repeated with different trial intervertebral devices until the appropriate height and lordotic angle are determined. An intervertebral device of height and lordotic angle corresponding to the chosen trial intervertebral device is then selected and mounted on an inserter instrument. The inserter instrument is used to insert the selected intervertebral device into the intervertebral space and the spinal fusion procedure is taken forward to its conclusion. It is to be noted that the trial intervertebral devices used for height and angle trials differ from the intervertebral devices implanted subsequently. Trial intervertebral devices are used only for trialling and not for implantation. This is because trial intervertebral devices are structured and bear surface markings for trialling purposes with such structure and markings being unsuited if not unsafe for implantation.

The first known approach to intervertebral device height and angle trials is often used for sizing of monolithic intervertebral devices. Sizing of a modular intervertebral device is, on the other hand, often carried out in accordance with a second known approach to height and angle trials. In contrast to a monolithic intervertebral device, a modular intervertebral device has superior and inferior endplates and is configured for change in separation height and in lordotic angle of the superior and inferior endplates, such as by way of insertion of a core between the superior and inferior endplates.

In the second known approach to height and angle trials, superior and inferior trial endplates are mounted on the end of an intervertebral device trial tool. This intervertebral device trial tool differs from the more simple, monolithic, intervertebral device trial tool used in the first known approach in that it is structured for manipulation by the surgeon to change separation height and lordotic angle between the superior and inferior trial endplates when the superior and inferior trial endplates are in situ in the intervertebral space. The surgeon changes the separation height and lordotic angle by way of the intervertebral device trial tool until the desired separation height and lordotic angle are achieved. The surgeon then determines the separation height and lordotic angle settings from x-ray inspection or reads off settings on the intervertebral device trial tool and uses the determined or read off settings to set the height and lordotic angle of a modular intervertebral device that is to be implanted in the intervertebral space. The thus height and angle configured modular intervertebral device is then inserted into the intervertebral space with an inserter instrument and the spinal fusion procedure is taken forward to its conclusion.

As per the first approach to height and angle trials, the superior and inferior trial endplates used in the second approach differ from the superior and inferior endplates of the modular intervertebral device implanted in the intervertebral space, it being noted that the superior and inferior trial endplates are unsuited for implantation. Although the second known approach to height and angle trials is usually for modular intervertebral devices, the second known approach may also be used for monolithic intervertebral devices. Considering this alternative application further, a monolithic intervertebral device of height and angle corresponding to the determined or read off settings is selected from a range of different monolithic intervertebral devices and is then inserted into the intervertebral space with an inserter instrument.

The present inventors have recognised the known approaches to height and angle trials to have shortcomings. The present invention has been devised in light of the inventors' appreciation of the above-mentioned shortcomings. It is therefore an object for the present invention to provide an improved approach to conducting height and angle trials for intervertebral devices.

Statement of Invention

According to a first aspect of the present invention there is provided an assembly for determining height and angle of an intervertebral device to be implanted in an intervertebral space, the assembly comprising:
a sizing instrument comprising a support attached to first and second arms which extend in generally a same direction from the support;
one of a superior endplate and an inferior endplate of the intervertebral device to be implanted engaging with a distal end of the first arm; and
the other of the superior endplate and the inferior endplate of the intervertebral device to be implanted engaging with a distal end of the second arm, the superior and inferior endplates opposing each other when they are engaged with their respective arms,
wherein the distal end of the second arm performs first and second forms of movement relative to the distal end of the first arm, the first and second forms of movement being independent of each other, the distal end of the second arm moving along different respective paths in the first and second forms of movement, the first form of movement changing separation between the superior and inferior endplates, the second form of movement changing an angle between the superior and inferior endplates,
wherein the support comprises a user control which is mechanically coupled to at least the second arm of the first and second arms to provide upon user operation of the user control each of the first and second forms of movement of the distal end of the second arm.

The present assembly is for determining height and angle, such as lordotic angle, of an intervertebral device to be implanted in an intervertebral space. The assembly comprises a sizing instrument and superior and inferior endplates of the intervertebral device to be implanted. A support of the sizing instrument supports first and second arms which extend in generally a same direction from the support. Each of the first and second arms may be attached at its proximal end to the support. One of the superior and inferior endplates of the intervertebral device to be implanted engages with a distal end of the first arm. The other of the superior and inferior endplates of the intervertebral device to be implanted engages with a distal end of the second arm. The relative disposition of the first and second arms is such that the superior and inferior endplates oppose each other when engaged with their respective arms. More specifically, the relative disposition of the first and second arms may be such that the superior and inferior endplates are in registration. The assembly may be brought into use by the surgeon mounting the superior and inferior endplates on their respective arms when the assembly is away from the patient and then inserting the superior and inferior endplates into the patient's intervertebral space by way of the sizing instrument. The surgeon may, for example, grip the support of the sizing instrument when inserting the superior and inferior endplates into the patient's intervertebral space. According to a first alternative approach, the assembly may be brought into use by mounting the superior and inferior endplates on a later described insertion instrument with the superior and inferior endplates being introduced into the intervertebral space by the insertion instrument and the sizing instrument being brought into engagement with the superior and inferior endplates while they are held in the intervertebral space by the insertion instrument. According to a second alternative approach, the assembly may be brought into use by mounting the superior and inferior endplates on the later described insertion instrument with the sizing instrument being brought into cooperation with the insertion instrument outside the patient's body. The superior and inferior endplates are then introduced to the into the intervertebral space by the combination of insertion instrument and sizing instrument with the sizing instrument engaging with the superior and inferior endplates while the superior and inferior endplates are held in the intervertebral space by the insertion instrument.

The distal end of the second arm performs first and second forms of movement of the distal end of the second arm relative to the distal end of the first arm. In view of each of the superior and inferior endplates engaging with a distal end of a respective one of the first and second arms, the other of the superior and inferior endplates engaging with the second arm performs the same first and second forms of movement relative to the one of the superior and inferior endplates engaged with the first arm. The first and second forms of movement are independent of each other. The distal end of the second arm moves along different respective paths in the first and second forms of movement with the first form of movement changing separation between the superior and inferior endplates and the second form of movement changing angulation between the superior and inferior endplates. The support comprises a user control which is mechanically coupled to at least the second arm of the first and second arms to provide upon user operation of the user control each of the first and second forms of movement of the distal end of the second arm. After the superior and inferior endplates have been inserted into the patient's intervertebral space, the surgeon operates the user control of the sizing instrument to cause the distal end of the second arm to perform the first and second forms of movement independently of each other whereby separation of the superior and inferior endplates, i.e. height, and angle of the superior and inferior endplates relative to each other, e.g. lordotic angle, may be adjusted independently of each other until a desired height and a desired angle are achieved.

As described above, the present assembly comprises the superior and inferior endplates of the intervertebral device to be implanted in the intervertebral space for which sizing trials are being carried out. This is in contrast to known approaches in which trial components, such as trial intervertebral devices or trial endplates, are used to determine height and angle with the trial components being set aside when height and angle have been determined and an intervertebral device of required height and angle being used for implantation. The present approach is contrary to firmly established practice of use of trial components for sizing and intervertebral devices for implantation. The present approach has the advantage of providing for, at the most, minimal loss of correspondence between height and angle as determined during sizing and height and angle of the implanted intervertebral device. The present inventors have become appreciative that the known approaches to sizing can result in loss of correspondence between height and angle determined during sizing and height and angle of the implanted intervertebral device sufficient to prejudice efficacy of the implanted intervertebral device.

The first arm may be attached to the support such that at least a part of the first arm is immovably attached to the support. More specifically, the first arm may be constituted such that the distal end engaging with the one of the superior and inferior endplates is immovable relative to the support whereby the engaged endplate does not move relative to the support. Change in separation and angle between the superior and inferior endplates may therefore be accomplished by movement of the distal end of the second arm.

The first arm may comprise an elongate first unitary member which extends from the support. A distal end of the first unitary member may constitute the distal end of the first arm.

A distal end of the first unitary member may be shaped to engage with the one of the superior and inferior endplates and more specifically may be shaped, such as by way of at least one formation, to inter-engage with the endplate. The distal end of the first unitary member may define at least one formation which is received in and moves along a respective keyway defined by the endplate. The keyway may be defined in a face of the endplate which faces a core of the intervertebral device when the core is inserted between the superior and inferior endplates. Furthermore, the keyway may extend from an anterior end of the endplate towards a posterior end of the endplate. The distal end of the first unitary member and the endplate may thus inter-engage with each other. More specifically, the distal end of the first unitary member and the endplate may thus inter-engage with each other to resist movement of the endplate relative to the first arm in a direction which is orthogonal to a longitudinal direction of the first arm and which is in a direction of separation of the first and second arms.

The distal end of the first unitary member may define first and second formations which are oppositely directed and which extend in a longitudinal direction of the first unitary member. The first and second formations may extend along the distal end of the first unitary member. The one of the superior and inferior endplates may define first and second keyways which face each other. The first formation may be received in and move along the first keyway and the second formation may be received in and move along the second keyway. The sizing instrument may thus attach to the endplate. Furthermore, resistance to movement of the endplate relative to the first arm may be presented in a direction which is orthogonal to a longitudinal direction of the first arm and orthogonal to a direction of separation of the first and second arms. There may therefore be minimal or substantially no movement of the endplate on the first unitary member in a side to side direction.

The first and second arms may be mounted on the support and may be constituted such that a long side of the first arm and a long side of the second arm are opposing.

As described above, the distal end of the second arm performs a first form of movement which changes separation between the distal end of the second arm and the distal end of the first arm. To provide the first form of movement, the second arm may be mounted towards its proximal end for rotation relative to the support. Where the first arm is mounted on the support as described above, the second arm may therefore rotate relative to the first arm as well as relative to the support. Furthermore, the second arm may be rotatably coupled to the first arm, and more specifically towards their proximal ends, whereby the second arm rotates relative to the first arm.

The second arm may rotate about an axis which is substantially orthogonal to a longitudinal direction of the second arm and substantially orthogonal to a direction of separation of the first and second arms.

Rotation of the second arm relative to the first arm, as described above, may cause the distal end of the second arm to be inclined to the distal end of the first arm with extent of inclination increasing with increasing separation of the first and second arms. Rotation of the second arm relative to the first arm may therefore increase separation of the superior and inferior endplates and also give rise to inclination of the superior and inferior endplates with increasing inclination as separation increases. The sizing instrument may be configured as described below such that rotation of the second arm relative to the first arm changes separation of the superior and inferior endplates whilst causing little or substantially no change in angle between the superior and inferior endplates.

The second arm may comprise a second unitary member, which is rotatably coupled towards its proximal end to the first arm such that the second unitary member extends from the support, and a third member assembly, which is rotatably coupled, such as by way of a hinge, at its proximal end to a distal end of the second unitary member. The third member assembly may rotate relative to the second unitary member about an axis which is substantially parallel to an axis of rotation of the second unitary member relative to the first arm. Rotatable coupling between the second unitary member and the third member assembly may provide for an angle between the distal end of the first arm and the third member assembly to be substantially unchanged as the angle between the second unitary member and the first arm changes.

Having rotatable coupling between the second unitary member and the third member assembly, as described above, may be insufficient for the angle between the distal end of the first arm and the third member assembly of the second arm to remain substantially unchanged with change in angle between the second unitary member of the second arm and the first arm. The distal end of the first arm and the third member assembly may therefore be mechanically coupled to each other to allow for movement together and apart of the distal end of the first arm and the third member assembly while resisting change in angle between the distal end of the first arm and the third member assembly.

The distal end of the first arm and the third member assembly may be coupled to each other by an extension mechanism which allows substantially only one degree of freedom of movement of distal end of the first arm and the third member assembly relative to each other.

The distal end of the first arm and the third member assembly may be mechanically coupled to each other by a scissors mechanism operative to change a separation between first and second ends of the scissors mechanism. The first end of the scissors mechanism may be mechanically coupled to the distal end of the first arm and the second, opposite end of the scissors mechanism may be mechanically coupled to the third member assembly.

The first arm may comprise an elongate support portion and an elongate movable portion. The elongate support portion may be immovably attached at its proximal end to the support and may engage with the endplate at its distal end, as described above. The elongate movable portion may be mounted for movement of the elongate movable portion relative to the elongate support portion and more specifically for relative movement in a longitudinal direction of the first arm. The elongate movable portion may therefore move away from and towards the support and also towards and away from the distal end of the elongate support portion. The elongate support portion may define a longitudinally extending channel in which the elongate movable portion is disposed and along which the elongate movable portion moves to thereby provide the relative movement.

An end of the elongate movable portion may be mechanically coupled to the extension mechanism described above and such that the extension mechanism extends as the elongate movable portion moves away from the support and contracts as the elongate movable portion moves towards the support.

The elongate movable portion may be mechanically coupled to the user control whereby user operation of the user control causes movement of the elongate movable portion. The user control may comprise a height adjustment control which upon user operation moves the elongate movable portion relative to the elongate support portion.

The height adjustment control may provide for progressive movement of the elongate movable portion. The height adjustment control may comprise a control knob and a threaded shaft which threadedly engages with the control knob. Rotation of the control knob causes linear movement of the threaded shaft in the longitudinal direction of the first arm. The threaded shaft may be mechanically coupled to the elongate movable portion whereby the threaded shaft pushes the elongate movable portion away from the support when the control knob is turned in a first direction and pulls the elongate movable portion towards the support when the control knob is turned in a second, opposite direction. Rotation of the control knob in the first direction causes linear movement of the threaded shaft towards the distal end of the first arm which in turn pushes the elongate movable portion away from the support with this in turn causing extension of the extension mechanism and thereby separation of the distal end of the second arm from the distal end of the first arm. Rotation of the control knob in the second, opposite direction causes linear movement of the threaded shaft away from the distal end of the first arm which in turn pulls the elongate movable portion towards the support with this in turn causing contraction of the extension mechanism and thereby movement of the distal end of the second arm towards the distal end of the first arm.

The support and the control knob may have indicator markings to indicate a position of the control knob relative to the support. The user may use the indicator markings to determine endplate to endplate height set by way of the sizing instrument.

As described above, the distal end of the second arm performs a second form of movement which changes the angle between the distal end of the second arm and the distal end of the first arm. To provide the second form of movement, the distal end of the second arm may comprise a tilting member which is mounted for change in extent of protrusion of the tilting member from a surface of the distal end of the second arm facing the endplate engaged with the second arm. Furthermore, the second arm may be mounted for movement relative to the support in a longitudinal direction of the second arm. Longitudinal movement of the second arm may change an extent of protrusion of the tilting member, e.g. from there being no protrusion to maximum extent of protrusion. When there is no protrusion of the tilting member, the tilting member may not push against the endplate whereby there is no angulation of the endplate relative to the endplate mounted on the first arm. When there is protrusion of the tilting member, the tilting member may bear against the endplate whereby an end of the endplate, such as an anterior end only of the anterior and posterior ends, is pushed away from the first arm to angle the endplate mounted on the second arm in relation to the endplate mounted on the first arm.

As described above, the second arm may comprise a second unitary member and a third member assembly. The third member assembly may comprise a first distal part and a second distal part. The first distal part may be coupled, and more specifically may be rotatably coupled, at its proximal end to the distal end of the second unitary member. Rotatable coupling of the first distal part to the second unitary member provides rotatable coupling of the third member assembly to the second unitary member. Furthermore, the second distal part may engage with the endplate, as described above. The tilting member may be mounted on the second distal part for rotation relative to the second distal part, rotation of the tilting member changing an extent to which an end of the tilting member protrudes from the second distal part. As described above, when there is protrusion of the tilting member, the tilting member may bear against the endplate whereby the endplate is pushed away from the first arm to angle the endplate mounted on the second arm in relation to the endplate mounted on the first arm. Furthermore, the first distal part may be mechanically coupled to the tilting member, and the first distal part may move relative to the second distal part, movement of the first distal part being in the longitudinal direction of the second arm. Longitudinal movement of the second unitary member may cause longitudinal movement of the first distal part relative to the second distal part which may rotate the tilting member by way of mechanical coupling between the first distal part and the tilting member. Rotation of the tilting member may change an extent to which the tilting member protrudes.

Mechanical coupling between the first distal part and the tilting member may be by way of a projection from the first distal part, and more specifically from a distal end of the first distal part, and a channel formed in the tilting member, the projection being received in the channel. As the first distal part moves in the longitudinal direction, the projection travels along the channel, and more specifically a channel which extends obliquely to a longitudinal axis of the arm, to thereby rotate the tilting member on the second distal part.

The second distal part may be held from moving in the longitudinal direction as the first distal part moves in the longitudinal direction relative to the second distal part. The second distal part may therefore be mechanically coupled to the distal end of the first arm to resist movement of the second distal part relative to the distal end of the first arm in the longitudinal direction. The second distal part may be mechanically coupled to the distal end of the first arm by the extension mechanism described above.

The support may comprise a trigger mechanism which is mechanically coupled to the second arm to cause longitudinal movement of the second arm upon operation of the trigger mechanism. A trigger mechanism has been found to afford improved control of angle adjustment compared with other mechanisms, such as a tab operated mechanism. The tab operated mechanism has a tab that extends from the side of the sizing instrument and which is moved linearly in the longitudinal direction to change the angle. The tab is moved by gripping the tab between the fingers or by pushing one side of the tab or pulling the other side of the tab by hand.

The trigger mechanism is comprised in the user control. As described above, the user control may comprise a height adjustment control, e.g. a control knob. The trigger mechanism and the height adjustment control may be operated by a user independently of each other whereby there is adjustment of height and adjustment of angle independently of each other.

As described above, the assembly is used for sizing trials which may involve selection of a core of desired height and angle from a range of cores of differing heights and angles. The assembly may therefore further comprise plural cores of differing heights and angles from which a selection is made upon completion of sizing trials.

According to the presently described approach, the endplates may be mounted on the sizing instrument such that the endplates are supported by the sizing instrument. In this approach, the sizing instrument is used to introduce the endplates into the intervertebral space to carry out a sizing trial. When the sizing trial is complete and height has been determined by reading from indicator markings on the support and angle has been determined by x-ray inspection, the sizing instrument is withdrawn from the intervertebral space with the superior and inferior endplates still mounted on the sizing instrument. The superior and inferior endplates are then removed from the sizing instrument and a core of appropriate height and angle is selected. The intervertebral device comprising superior and inferior endplates and the selected core is then implanted using an inserter instrument of known form.

As described above, an endplate may inter-engage with the distal end of the first arm whereby the endplate is supported by the first arm whereby the thus supported endplate may be introduced to the intervertebral space.

As described above, an endplate engages with the distal end of the second arm of the sizing instrument. When the endplate is supported by an insertion instrument, as described below in accordance with the alternative approach, engagement is in the sense of the distal end, or a part thereof, of the second arm bearing against the endplate whereby height and angle are changed. In the presently described approach, both endplates are supported by the first and second arms of the sizing instrument. Engagement of the endplate with the second arm in the sense of the second arm merely bearing against the endplate is insufficient to support the endplate on the second arm to allow its introduction into the intervertebral space. Therefore, the second arm of the sizing instrument may be structured differently for use in the presently described approach such that the endplate is supported by the second arm. The different structure of the second arm in this regard will now be described.

A distal end of the second arm may be shaped, such as by way of at least one formation, to inter-engage with the endplate. Where the second arm comprises the third member assembly described above, the at least one formation may be comprised in the third member assembly. The endplate and the distal end of the second arm may define first and second sets of formations.

The first set of formations may provide for inter-engagement between the endplate and the second arm at a location further away from the support than the location where the second set of formations provide for inter-engagement between the endplate and the second arm. The first set of formations may provide for inter-engagement towards the posterior end of the endplate and the second set of formations may provide for inter-engagement towards the anterior side of the endplate.

The first set of formations may comprise a recess defined in the endplate with the recess extending in the transverse direction, i.e. orthogonal to the anterior-posterior direction and orthogonal to a direction of separation of the distal ends of the first and second arms. The first set of formations may further comprise a protrusion, such as an elongate and transversely extending protrusion, which protrudes from the distal end of the second arm. When the endplate is slidably engaged with the distal end of the second arm, the protrusion is received in the recess to thereby present resistance to separation of the endplate from the second arm at the first set of formations.

Furthermore, the first set of formations may have cooperating profiles which allow for rotation of the endplate at the first set of formations relative to the distal end of the second arm. The posterior end of the endplate may thus be held with minimal movement relative to the distal end of the second arm, aside from rotation, while the anterior end of the endplate moves during angle adjustment.

The second set of formations may comprise at least one keyway defined in the anterior face of the endplate and which extends towards the posterior end of the endplate. More specifically, the second set of formations may comprise first and second such keyways which face each other. The first keyway may be towards a first transverse side of the endplate and the second keyway may be towards a second transverse side of the endplate.

The second set of formations may further comprise at least one protrusion which extends transversely from the distal end of the second arm. When the endplate is slidably engaged with the distal end of the second arm, the transversely extending protrusion is received in the keyway to thereby present resistance to separation of the endplate from the second arm at the second set of formations. Where the second set of formations comprises first and second keyways, the second set of formations may comprise first and second such protrusions which extend in opposite directions. In use, the first and second protrusions inter-engage respectively with the first and second keyways.

Where the second arm comprises the third member assembly, as mentioned above, the protrusion of the first set of formations may be comprised in the second distal part of the third member assembly and the protrusion of the second set of formations may be comprised in the tilting member of the third member assembly. The first and second sets of protrusions hold the endplate on the distal end of the second arm with the second set of protrusions holding the endplate as the endplate angle is changed by rotation of the tilting member.

The assembly may be used according to an alternative approach. According to the alternative approach, the superior and inferior endplates are introduced to and are held in the intervertebral space by means other than the sizing instrument. The distal ends of the first and second arms of the sizing instrument are then introduced to the intervertebral space and such that the first and second arms engage with the two endplates. The sizing instrument is then used as described above to determine height and angle. When the sizing trial is complete, the sizing instrument is disengaged from the endplates and withdrawn from the intervertebral space while the endplates remain held in the intervertebral space. A core of appropriate height and angle is then selected. The selected core is then inserted by way of a core inserter instrument between the superior and inferior endplates being held in the intervertebral space.

In the alternative approach, superior and inferior endplates may be introduced into and held in the intervertebral space by an insertion instrument. The present assembly may comprise the insertion instrument. The insertion instrument and its use in conjunction with the sizing instrument are described below.

The distal end of the second arm of the sizing instrument may lack the protrusions of the first and second sets of formations described above in respect of the previously described approach.

The endplate may have the same form as the endplate described above in respect of the previously described approach. The endplate may therefore have the recess and the at least one keyway of the first and second sets of formations described above in respect of the previously described approach.

The insertion instrument may comprise at least one superior insertion arm, and more specifically a pair of superior insertion arms, and at least one inferior insertion arm, and more specifically a pair of inferior insertion arms.

The at least one superior insertion arm may be mounted on a superior insertion support such that the at least one superior insertion arm extends from the superior insertion support. Where there is a pair of superior insertion arms, the superior insertion arms may be spaced apart and may extend generally parallel with each other. The superior insertion arms may be spaced apart in the transverse direction.

The at least one inferior insertion arm may be mounted on an inferior insertion support such that the at least one inferior insertion arm extends from the inferior insertion support. Where there is a pair of inferior insertion arms, the inferior insertion arms may be spaced apart and may extend generally parallel with each other. The inferior insertion arms may be spaced apart in the transverse direction.

The superior insertion support and the inferior insertion support may be mechanically coupled to each other whereby: the at least one superior insertion arm and the at least one inferior insertion arm extend in generally a same direction such that, in use, the distal end of the at least one superior insertion arm and the distal end of the at least one inferior insertion arm engage at a respective location in a side, and more specifically an anterior side, of a respective one of the superior and inferior endplates; and the superior and inferior insertion supports rotate relative to each other to rotate the at least one superior insertion arm and the at least one inferior insertion arm relative to each other. The superior insertion arm may be unarticulated between its distal end and the superior insertion support, and the inferior insertion arm may comprise a hinge between its distal end and the inferior insertion support, the hinge providing for rotation of the distal end of the inferior insertion arm towards or away from the superior arm.

The distal end of each of the at least one superior insertion arm of the insertion instrument may be received in a respective bore formed in a side of the endplate, such as in an anterior side of a superior endplate. The distal end of each of the at least one inferior insertion arm may be received in a respective bore formed in a side of an endplate, such as in an anterior side of an inferior endplate. The superior and inferior endplates may thus be mounted on and supported by the insertion instrument. The insertion instrument may then be used to introduce the endplates into the intervertebral space.

The sizing instrument may be brought into use by inserting the distal end of the sizing instrument, i.e. the distal end of the at least one superior insertion arm and the distal end of the at least one inferior insertion arm, between the superior and inferior insertion supports. The sizing instrument may then be pushed further such that the distal end of the sizing instrument travels between and along the at least one superior insertion arm and the at least one inferior insertion arm of the insertion instrument.

The first arm of the sizing instrument and the superior insertion support may define cooperating surface profiles whereby the first arm of the sizing instrument may be moved in the longitudinal direction relative to the superior insertion support during insertion of the sizing instrument while resistance to separation of the first arm and the superior insertion support is presented in at least one direction orthogonal to the longitudinal direction. For example, the superior insertion support may define two facing and longitudinally extending channels and the first arm of the sizing instrument may define two longitudinally extending protrusions which protrude from opposite sides of the first arm, with each of the two longitudinally extending protrusions being received in a respective one of the longitudinally extending channels.

The at least one superior insertion arm may be formed similarly to the superior insertion support. More specifically, the at least one superior insertion arm may define two facing and longitudinally extending channels. During insertion of the sizing instrument, each of the two longitudinally extending protrusions of the first arm may be received in a respective one of the longitudinally extending channels of the at least one superior insertion arm. Each of the longitudinally extending channels of the at least one superior insertion arm may be in registration with a respective one of the longitudinally extending channels of the superior insertion support.

When the first and second arms of the sizing instrument are received fully between the superior and inferior insertion arms of the insertion instrument, the distal ends of the arms of the sizing instrument may engage with each respective endplate.

More specifically, the distal end of the first arm of the sizing instrument may slidably inter-engage with one of the endplates, as described above. Also, the distal end of the second arm of the sizing instrument may be disposed relative to the other endplate such that it bears against, and thereby engages with, the other endplate during the sizing process.

Sizing may be carried out as described above with respect to the previously described approach. For example, the trigger mechanism and the height adjustment control of the sizing instrument may be operated by a user independently of each other whereby there is adjustment of height and adjustment of angle independently of each other.

When the sizing process is complete, the sizing instrument may be withdrawn from between the at least one superior insertion arm and the at least one inferior insertion arm of the insertion instrument with the insertion instrument continuing to hold the superior and inferior endplates in the intervertebral space during and after withdrawal of the sizing instrument.

When a core of appropriate height and angle has been selected based on the height and angle determined during the sizing process, the selected core may be inserted between the between the at least one superior insertion arm and the at least one inferior insertion arm of the insertion instrument at the superior and inferior insertion supports. More specifically, the selected core may be inserted between the superior and inferior insertion supports. The present assembly may comprise at least one core from which a selection is made.

The selected core may then be pushed along the superior and inferior insertion arms, such as by a core inserter, until the selected core reaches the superior and inferior endplates held by the insertion instrument. The selected core may then be finally pushed, such as by the core inserter, between the superior and inferior endplates until the selected core is received properly between the superior and inferior endplates. The present assembly may comprise the core inserter.

The selected core and the superior insertion support may define cooperating surface profiles whereby the selected core may be moved in the longitudinal direction relative to the superior insertion support during insertion of the selected core while resistance to movement of the selected core relative to the superior insertion support is presented in at least one direction orthogonal to the longitudinal direction. For example, the superior insertion support may define two facing and longitudinally extending channels and the selected core may define two longitudinally extending protrusions which protrude from opposite sides of the selected core, with each of the two longitudinally extending protrusions being received in and moving along a respective one of the longitudinally extending channels.

The at least one superior insertion arm may be formed as described above whereby the at least one superior insertion arm defines two facing and longitudinally extending channels. During insertion of the selected core, each of the two longitudinally extending protrusions of the selected core may be received in and move along a respective one of the longitudinally extending channels of the at least one superior insertion arm.

The core inserter may comprise a core inserter support and an elongate member which is movable through the core inserter support. The elongate member may be movable through the core inserter support by, for example, threaded engagement between elongate member and core inserter support. The core inserter support may be removably mounted on the insertion instrument, such as on the superior insertion support, and such that the elongate member is directed between the at least one superior insertion arm and the at least one inferior insertion arm of the insertion instrument. A user, such as a surgeon, may move the elongate member through the core inserter support to increase an extent to which the elongate member is received between the at least one superior insertion arm and the at least one inferior insertion arm of the insertion instrument. An end of the elongate member between the at least one superior insertion arm and the at least one inferior insertion arm may bear against the selected core to thereby push the selected core towards the superior and inferior endplates held by the insertion instrument.

According to a second aspect of the present invention, there is provided a method of determining height and angle of an intervertebral device to be implanted in an intervertebral space by way of an assembly comprising a superior endplate of the intervertebral device, an inferior endplate of the intervertebral device and a sizing instrument, the sizing instrument comprising a support, which supports first and second arms which extend in generally a same direction from the support, the support comprising a user control which is mechanically coupled to at least the second arm of the first and second arms, the method comprising:
  bringing one of the superior endplate and the inferior endplate into engagement with a distal end of the first arm of the sizing instrument;
  bringing the other of the superior endplate and the inferior endplate into engagement with a distal end of the second arm of the sizing instrument, the superior and inferior endplates opposing each other when they are engaged with their respective arms; and
  operating the user control to cause the distal end of the second arm to perform first and second forms of movement relative to the distal end of the first arm, the first and second forms of movement being independent of each other, the distal end of the second arm moving along different respective paths in the first and second forms of movement, the first form of movement changing separation between the superior and inferior endplates, the second form of movement changing an angle between the superior and inferior endplates.

As described above, the sizing instrument may be used with or without the insertion instrument. Without the insertion instrument, the second arm of the sizing instrument is structured as described above to support an endplate and the sizing instrument is used alone to conduct a sizing trial. With the insertion instrument, the endplates may be introduced to and held in the intervertebral space by the insertion instrument. The sizing instrument is then brought into use in conjunction with the insertion instrument as described above.

Further embodiments of the second aspect of the present invention may comprise one or more features of the first aspect of the present invention.

According to a third aspect of the present invention there is provided a sizing instrument for determining height and angle of an intervertebral device to be implanted in an intervertebral space, the sizing instrument comprising:
  a support comprising a user control; and
  first and second arms supported on the support and extending in generally a same direction from the support, a distal end of the first arm being configured to engage with one of a superior endplate and an inferior endplate, a distal end of the second arm being configured to engage with the other of the superior endplate and the inferior endplate, the superior and inferior endplates opposing each other when they are engaged with their respective arms,
  wherein the user control comprises a trigger mechanism and a height adjustment control, the trigger mechanism and the height adjustment control being user operable independently of each other,
  wherein the height adjustment control is mechanically coupled to at least the second arm of the first and second arms, user operation of the height adjustment control causing the distal end of the second arm to perform a first form of movement relative to the distal end of the first arm to thereby change separation between the distal ends of the first and second arms, and
  wherein the trigger mechanism is mechanically coupled to at least the second arm of the first and second arms, user operation of the trigger mechanism causing the distal end of the second arm to perform a second form of movement relative to the distal end of the first arm to change an angle between the distal end of the first arm and the distal end of the second arm.

Operation of the height adjustment control causes the distal end of the second arm to perform a first form of movement relative to the distal end of the first arm to thereby change separation between the distal ends of the first and second arms. When the superior and inferior endplates are engaged with their respective distal ends, the first form of movement results in change in separation between the superior and inferior endplates. Operation of the trigger mechanism causes the distal end of the second arm to perform a second form of movement relative to the distal end of the first arm to change an angle between the distal end of the first arm and the distal end of the second arm. When the superior and inferior endplates are engaged with their respective distal ends, the second form of movement results in change in angle between the superior and inferior endplates.

The inventors have found the trigger mechanism to afford better user control of angle than, for example, a control knob, as described above in respect of height adjustment, or the tab operated mechanism described above.

The superior endplate may be one of a superior endplate of the intervertebral device to be implanted and a superior trial plate. The latter may be used for sizing only and not implantation. The inferior endplate may be one of an inferior endplate of the intervertebral device to be implanted and an inferior trial plate. The latter may be used for sizing only and not implantation.

Further embodiments of the third aspect of the present invention may comprise one or more features according to the first aspect of the present invention.

BRIEF DESCRIPTION OF DRAWINGS

Further features and advantages of the present invention will become apparent from the following specific description, which is given by way of example only and with reference to the accompanying drawings, in which:

FIG. 3A is view around the support of the assembly of FIG. 1 with the control knob removed;

FIG. 3B is view of what is shown in FIG. 3A from a different perspective;

DESCRIPTION OF EMBODIMENTS

Figure 1:
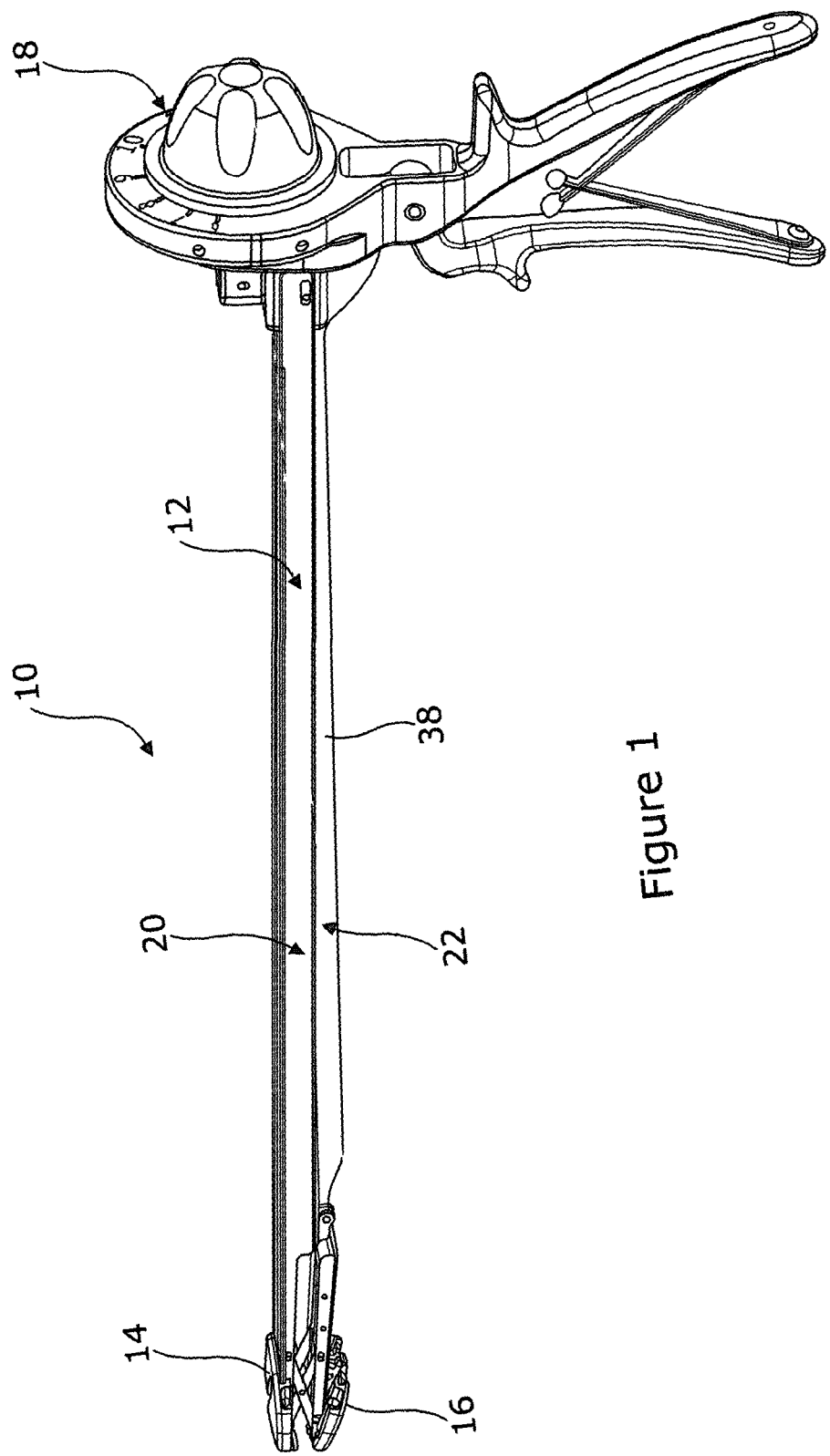
FIG. 1 is a perspective view of an assembly for determining height and lordotic angle according to a first embodiment of the present invention.

A perspective view of an assembly 10 for determining height and lordotic angle according to a first embodiment of the present invention is shown in FIG. 1. The assembly 10 of FIG. 1 comprises a sizing instrument 12 and superior 14 and inferior 16 endplates of an intervertebral device to be implanted in an intervertebral space. The sizing instrument 12 comprises a support 18 on which first 20 and second 22 arms are supported such that they extend in generally a same direction from the support. Each of the first and second arms 20, 22 is attached at its proximal end to the support 18. The superior endplate 14 is mounted on a distal end of the first arm 20. The inferior endplate 16 is mounted on a distal end of the second arm 22. The relative disposition of the first and second arms 20, 22 is such that the superior and inferior endplates 14, 16 are in registration with each other with their core facing surfaces opposing each other.

Figure 2A:
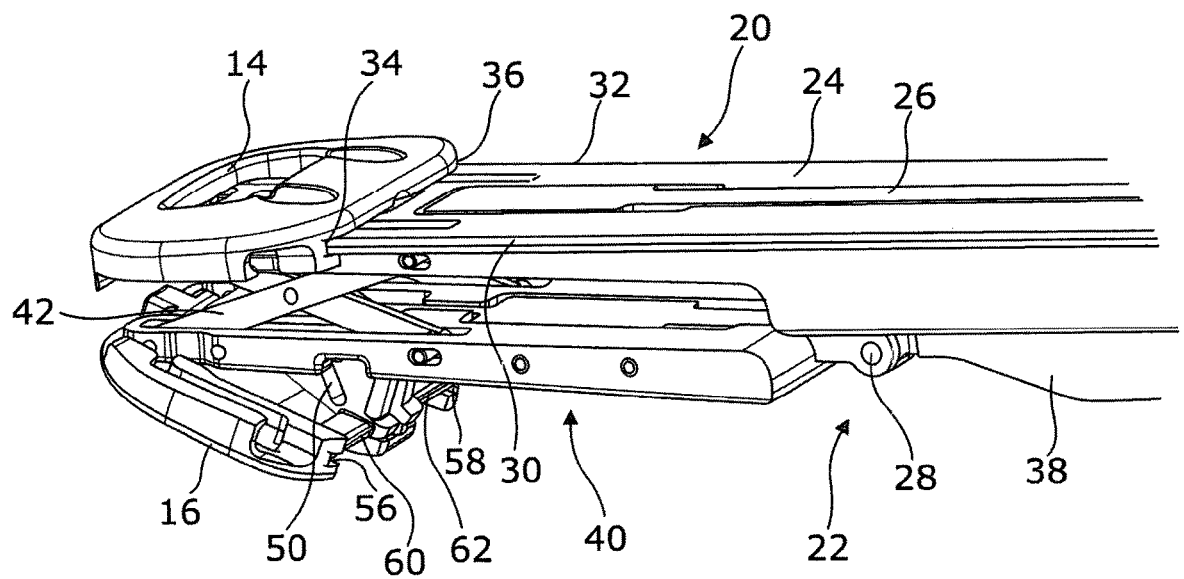
FIG. 2A shows the distal end of the assembly of FIG. 1.
Figure 2B:
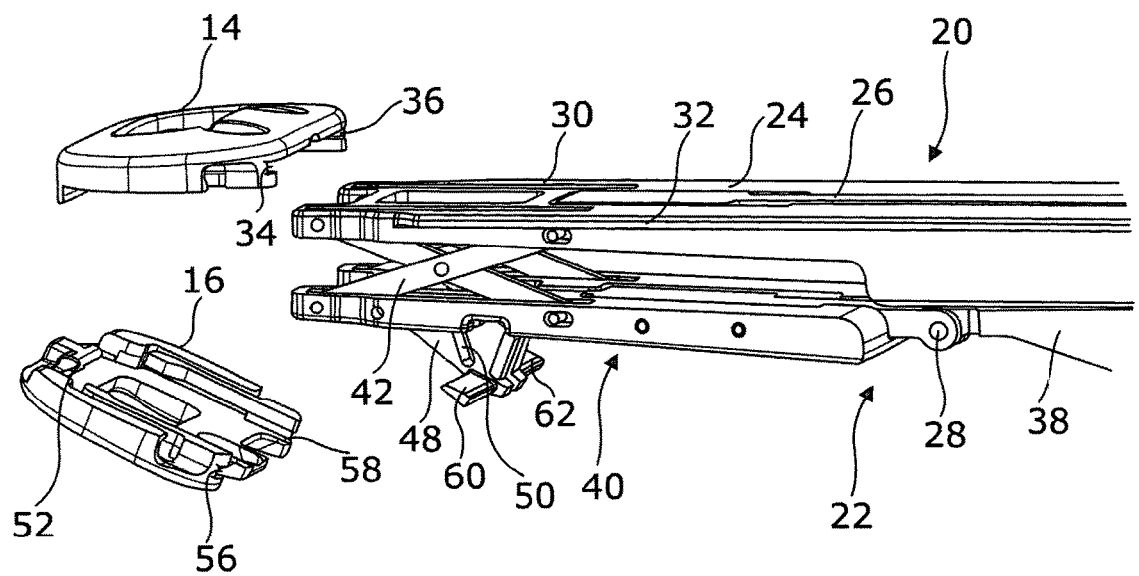
FIG. 2B shows the distal end of the assembly of FIG. 1 with the superior and inferior endplates removed.
Figure 2C:
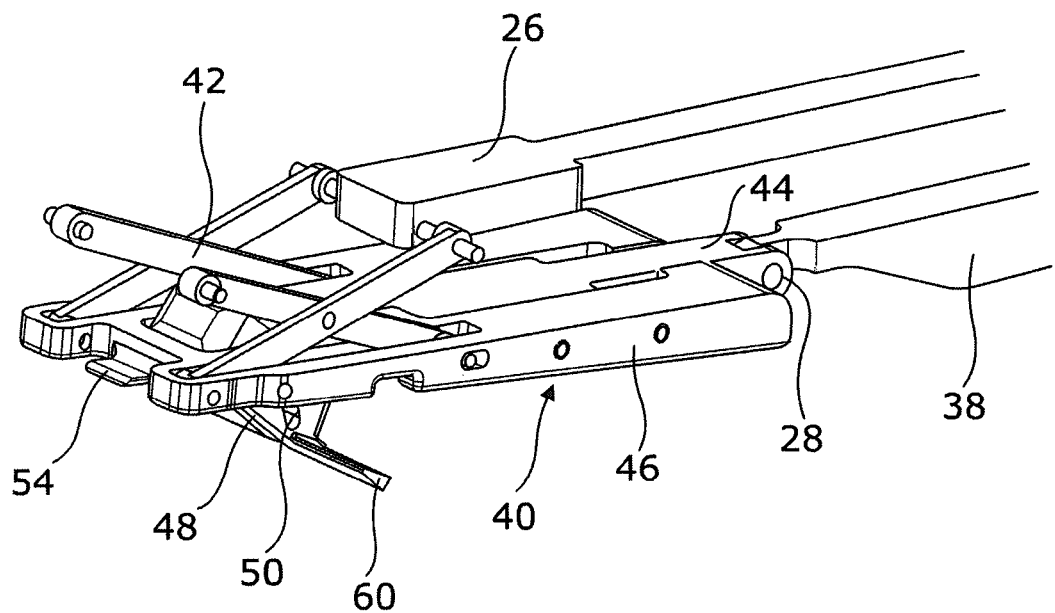
FIG. 2C is the same view as FIG. 2B with the first arm removed.
Figure 2D:
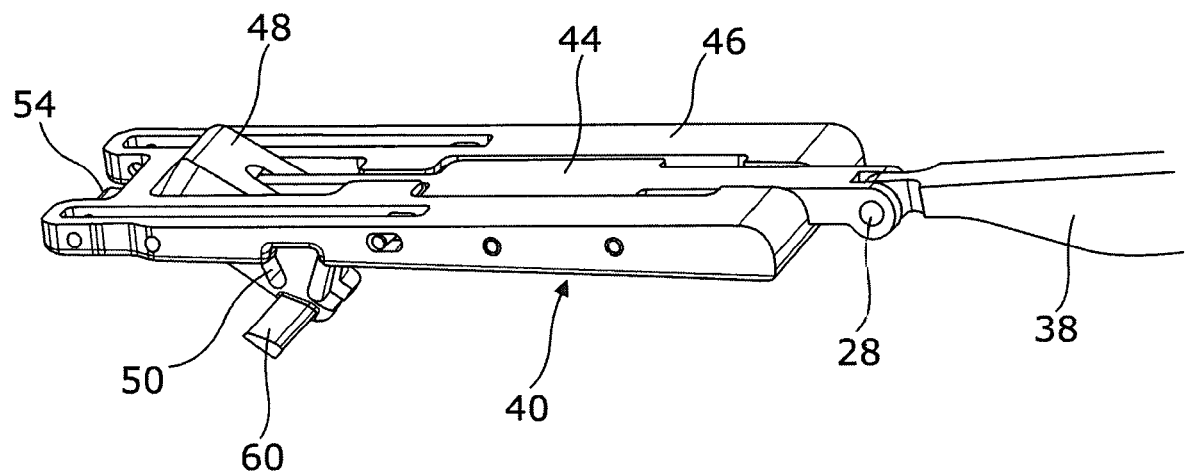
FIG. 2D is the distal end as shown in FIG. 2C with the scissors mechanism removed and from a different perspective.

The first and second arms 20, 22 of the first embodiment will now be described with reference to the more detailed views of FIGS. 2A to 2D. FIG. 2A shows the distal end of the assembly of FIG. 1. FIG. 2B shows the distal end of the assembly of FIG. 1 with the superior and inferior endplates 14, 16 removed. FIG. 2C is the same view as FIG. 2B with part of the first arm removed. FIG. 2D is the distal end as shown in FIG. 2C with all of the first arm and the scissors mechanism removed and from a different perspective.

The first arm 20 comprises an elongate support portion 24 and an elongate movable portion 26. The elongate support portion 24 is attached at its proximal end to the support 18. The distal end of the elongate support portion 24 is shaped to inter-engage with the superior endplate 14. As can be seen from FIGS. 2A and 2B, the elongate support portion 24 defines first and second linear projections 30, 32 (which constitute first and second formations) which are oppositely directed and which extend along the sides of the elongate support portion 24 in a longitudinal direction of the first arm. The superior endplate 14 defines on its core facing surface first and second keyways 34, 36 which face each other and which extend from the anterior end of the endplate towards the posterior end. The first linear projection 30 is received in and moves along the first keyway 34 and the second linear projection 32 is received in and moves along the second keyway 36. The superior endplate 14 is thus attached to and held by the sizing instrument 12. Inter-engagement of linear projections 30, 32 with keyways 34, 36 presents resistance to movement of the superior endplate 14 relative to the first arm 20 in a first direction, which is orthogonal to the longitudinal direction of the first arm and in a direction of separation of the first and second arms, and in a second direction, which is orthogonal to the longitudinal direction of the first arm and orthogonal to a direction of separation of the first and second arms.

As described in more detail below with reference to FIGS. 3A and 3B, the second arm 22 is rotatably coupled towards its proximal end to the first arm 20 and more specifically towards the proximal end of the first arm. In view of the first arm 20 being immovably mounted on the support 18, the second arm 22 therefore rotates relative to the first arm and the support 18. The second arm 22 rotates about an axis which is substantially orthogonal to a longitudinal direction of the second arm and substantially orthogonal to a direction of separation of the first and second arms. The second arm 22 comprises a second unitary member 38, which is rotatably mounted towards its proximal end on the first arm to provide the rotatable coupling of the second arm described earlier in the present paragraph. The second arm 22 also comprises a third member assembly 40, which is rotatably coupled by way of a hinge 28 at its proximal end to a distal end of the second unitary member 38. The third member assembly 40 rotates relative to the second unitary member 38 about an axis of the hinge 28 which is substantially parallel to the axis of rotation of the second unitary member 38 relative to the first arm 20. Rotatable coupling between the second unitary member 38 and the third member assembly 40 allows for an angle between the distal end of the first arm 20 and the third member assembly 40 to remain unchanged with change in angle between the second unitary member 38 and the first arm 20. Therefore, if the distal end of the first arm 20 is parallel with the third member assembly 40, upon rotation of the second unitary member 38 of the second arm 22 away from the first arm 20 to increase separation between the superior and inferior endplates 14, 16, the hinge 28 between the second unitary member 38 and the third member assembly 40 allows the distal end of the first arm 20 to remain parallel with the third member assembly 40.

Referring again to FIGS. 2A and 2B, the third member assembly 40 is supported by a scissors mechanism 42 having first and second ends. The first end of the scissors mechanism 42 is mechanically coupled to the distal end of the elongate support portion 24 of the first arm 20 and the second, opposite end of the scissors mechanism is mechanically coupled to the third member assembly 40. The scissors mechanism 42 allows for only one degree of freedom of movement of the distal end of the elongate support portion 24 of the first arm 20 and the third member assembly 40 relative to each other, i.e. either movement together or movement apart.

The elongate movable portion 26 is mounted for movement of the elongate movable portion relative to the elongate support portion 24 in a longitudinal direction of the first arm. The elongate support portion 24 defines a longitudinally extending channel in which the elongate movable portion 26 is received and along which the elongate movable portion moves to thereby provide the relative movement. As described in more detail below with reference to FIGS. 3A and 3B, a first end of the elongate movable portion 26 is mechanically coupled to the control knob of the user control 18. The second, opposite end of the elongate movable portion 26 is mechanically coupled to arms of the scissors mechanism 42. Rotation of the control knob by the user pushes the elongate movable portion 26 along the channel defined by the elongate support portion 24 and away from the support 18 with resulting movement of the second end of the elongate movable portion driving the arms of the scissors mechanism 42 such that the scissors mechanism extends. Extension of the scissors mechanism 42 pushes the third member assembly 40 away from the distal end of the first arm 20 to thereby increase height. Conversely, rotation of the control knob by the user in the opposite direction pulls the elongate movable portion 26 along the channel defined by the elongate support portion 24 and towards the support 18 with resulting movement of the second end of the elongate movable portion driving the arms of the scissors mechanism 42 such that the scissors mechanism contracts. Contraction of the scissors mechanism 42 pulls the third member assembly 40 towards the distal end of the first arm 20 to thereby reduce height. As discussed above, the scissors mechanism 42 and the hinge 28 work together to keep the third member assembly 40 generally parallel with the distal end of the first arm 20 as the second unitary member 38 rotates relative to the first arm during height adjustment.

Referring now in particular to FIGS. 2C and 2D, the third member assembly 40 comprises a first distal part 44 and a second distal part 46 which are coupled to each other for movement of the first distal part relative to the second distal part in the longitudinal direction. The first distal part 44 is rotatably coupled by hinge 28 at its proximal end to the distal end of the second unitary member 38 to provide the rotatable coupling of the third member assembly 40 and second unitary member 38 described above. As described in more detail below, the second distal part 46 is shaped to inter-engage with the inferior endplate 16 whereby the inferior endplate is supported by the second distal part. A tilting member 48 is mounted for rotation on the second distal part 46 about an axis that is substantially parallel to the axis of rotation of hinge 28. The distal end of the first distal part 44 defines two oppositely directed protrusions which are received in respective channels 50 defined in the tilting member 48. The channels 50 are inclined to the longitudinal axis of the second arm. Movement of the first distal part 44 relative to the second distal part 46 causes the protrusions on the first distal part to travel along the channels 50 to thereby rotate the tilting member 48. Rotation of the tilting member 48 causes the tilting member 48 protrude from the second distal part 44 and to bear against the supported inferior endplate and to push the anterior end of the inferior endplate away from the distal end of the first arm.

As mentioned above, the second distal part 46 is shaped to inter-engage with the inferior endplate 16 whereby the inferior endplate is supported by the second distal part. The inferior endplate is supported by means of first and second sets of formations defined by the inferior endplate 16 and the second distal part 46.

The first set of formations comprises a transversely extending recess 52, which is defined in the core facing side of the inferior endplate 16 towards the posterior end of the inferior endplate and such that the recess faces towards the anterior end of the inferior endplate. The first set of formations further comprises an elongate transversely extending protrusion 54, which protrudes from the distal end of the second distal part 46. When the inferior endplate 16 is slidably engaged with the second distal part 46, the protrusion 54 is received in the recess 52 to thereby present resistance to separation of the endplate from the second arm at the first set of formations. The first set of formations therefore provides for inter-engagement between the inferior endplate 16 and the second distal part 46 towards the posterior end of the inferior endplate. Further to this, the recess 52 and the protrusion 54 have cooperating profiles which allow for rotation of the protrusion relative to the recess while the protrusion remains received in the recess. The posterior end of the inferior endplate is thus held with minimal movement towards or away from the distal end of the second arm while the anterior end of the endplate moves during angle adjustment.

The second set of formations comprises first and second keyways 56, 58 which are defined in the anterior end of the inferior endplate 16 and which extend towards the posterior end of the inferior endplate such that the first and second keyways face each other. The first keyway 56 is towards a first transverse side of the inferior endplate and the second keyway 58 is towards a second transverse side of the inferior endplate. The second set of formations further comprises first and second protrusions 60, 62 which extend transversely from opposite sides of the tilting member 48 of the third member assembly 40. When the inferior endplate 16 is slidably engaged with the second distal part 46 of the second arm, the first and second protrusions 60, 62 are received respectively in the first and second keyways 56, 58 whereby the anterior end of the inferior endplate 16 inter-engages with the third member assembly 40. The first and second sets of protrusions hold the inferior endplate 16 on the distal end of the second arm 22 with the second set of protrusions holding the anterior end of the inferior endplate as the inferior endplate angle is changed by rotation of the tilting member 48.

The second distal part 46 is held from moving in the longitudinal direction by the scissors mechanism 42 as the first distal part 44 moves in the longitudinal direction relative to the second distal part 46. Considering the scissors mechanism 42 further, the second end of the scissors mechanism 42 is mechanically coupled to the second distal part 46. Further to being mounted for rotation on the first arm 20, the second unitary member 38 is mounted for movement relative to the support in the longitudinal direction. As described further below with reference to FIGS. 3A and 3B, the second unitary member 38 is moved in the longitudinal direction by a trigger mechanism mounted on the support 18. When the second unitary member 38 is moved longitudinally by the trigger mechanism it moves the first distal part 44 in the longitudinal direction relative to the second distal part 46 with movement of the second distal part 46 causing rotation of the tilting member 48, as described above. Operation of the trigger mechanism thus rotates the tilting member 48 to thereby control the inclination of the inferior endplate 16 and hence the lordotic angle between the superior and inferior endplates 14, 16.

A view around the support of the assembly of FIG. 1 is shown in FIGS. 3A and 3B. FIG. 3A shows the control knob of the support removed and displaced to the right.

As described above, height adjustment is achieved by movement of the elongate movable portion 26 along the longitudinally extending channel defined by the elongate support portion 24. As also described above, the first proximal end of the elongate movable portion 26 is mechanically coupled to the control knob 70 of the user control 18 to provide for movement of the elongate movable portion 26 along the longitudinally extending channel upon rotation of the control knob. Considering FIG. 3A, a threaded shaft 72 extends from the first and second arm side of the support 18 to the control knob 70 side of the support. On the control knob 70 side of the support, the threaded shaft 72 threadedly engages with a bore defined in the control knob. Rotation of the control knob 70 in a first direction moves the threaded shaft 72 towards the distal end of the first arm. Rotation of the control knob 70 in a second opposite direction moves the threaded shaft 72 away from the distal end of the first arm such that more of the threaded shaft is received in the bore defined by the control knob 70. The threaded shaft 72 is attached on the first and second arm side of the support 18 to the elongate movable portion 26. Rotation of the control knob 70 in the first direction therefore pushes the elongate movable portion 26 away from the support 18 and rotation of the control knob in the second direction pulls the elongate movable portion 26 towards the support. The control knob 70 therefore provides for progressive movement of the elongate movable portion 26 and as a result progressive change in height.

As described above, the scissors mechanism 42 extends and contracts and in doing so moves the third member assembly 40 respectively away from and towards the distal end of the first arm 20. Further as described above, movement of the third member assembly 40 away from and towards the distal end of the first arm 20 causes rotation of the second unitary member 38 relative to the first arm 20 about a coupling near the support 18. Considering FIG. 3A, the proximal end of the second unitary member 38 comprises an axle member 74 which is received at each opposite end of the axle member in a slot defined in the elongate support portion 24 of the first arm 20 to thereby provide for rotation of the second unitary member relative to the first arm.

As shown in FIG. 1, the support 18 and the control knob 70 have indicator markings to indicate a position of the control knob relative to the support. The user uses the indicator markings to determine endplate to endplate height set by way of rotation of the control knob.

As described above, angle adjustment is achieved by the second unitary member 38 being moved in the longitudinal direction by the trigger mechanism 78 mounted on the support 18. When the second unitary member 38 is moved longitudinally by the trigger mechanism 78 it moves the first distal part 44 in the longitudinal direction relative to the second distal part 46 with such relative movement of the first distal part 44 causing rotation of the tilting member 48. Operation of the trigger mechanism thus rotates the tilting member 48 to thereby control the inclination of the inferior endplate 16 and hence the lordotic angle between the superior and inferior endplates 14, 16. Considering FIGS. 3A and 3B, when the trigger mechanism 78 is operated, a first one of the trigger mechanism's arms 80 rotates relative to the other arm 82 of the trigger mechanism about a trigger mechanism hinge 84. A proximal end 86 of the first trigger mechanism arm 80 is coupled to a spur 88 extending from the proximal end of the second unitary member 38. As the proximal end 86 rotates upon operation of the trigger mechanism 78, cooperation of the proximal end with the spur 88 pushes or pulls the second unitary member 38 in the longitudinal direction to thereby rotate the tilting member 48 and cause a change in angle. As the second unitary member 38 moves in the longitudinal direction, the axle member 74 towards the proximal end of the second unitary member travels forwards and backwards in the slots defined in the elongate support portion 24 of the first arm 20.

The assembly of FIG. 1 is brought into use by fitting the superior and inferior endplates 14, 16 to the distal end of the sizing instrument 12 as described above. The surgeon then grips the support 18 and introduces the superior and inferior endplates 14, 16 into the intervertebral space. Sizing trials in respect of height and angle are then carried out by operating the control knob 70 and the trigger mechanism 78 as described above. When desired height and angle have been achieved, the height is read off from the markings on the control knob 70 and the support and the angle is determined by x-ray inspection or the like. The sizing instrument 12 is then withdrawn from the intervertebral space and a core of determined height and angle is selected. The superior and inferior endplates 14, 16 are removed from the sizing instrument 12 and the superior and inferior endplates are implanted in the intervertebral space with the selected core by means of a tool of known form and function.

Figure 4:
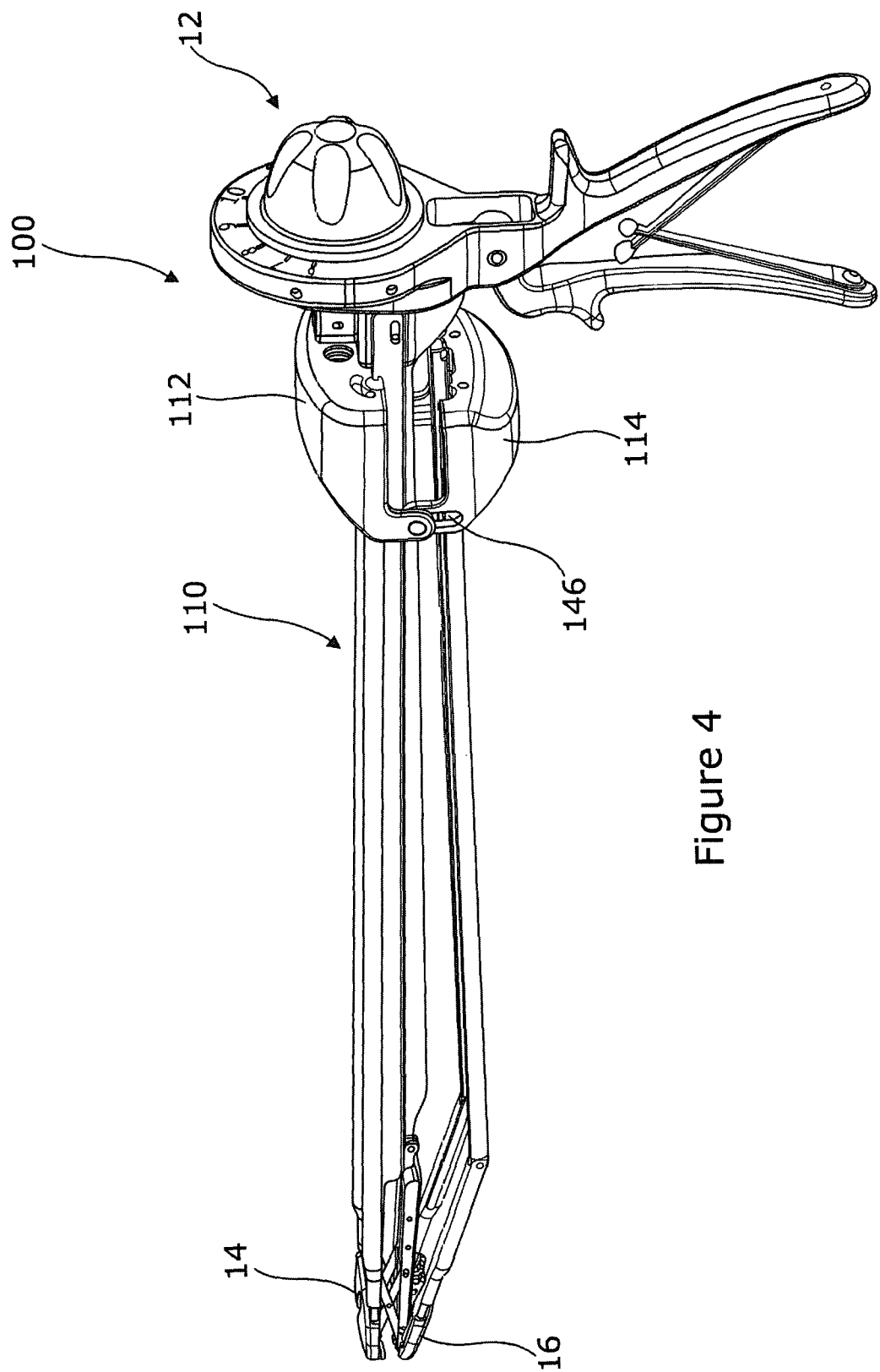
FIG. 4 is a perspective view of an assembly for determining height and lordotic angle according to a second embodiment of the present invention.

A perspective view of an assembly 100 for determining height and lordotic angle according to a second embodiment of the present invention is shown in FIG. 4. The second embodiment is intended for use in anterior lumbar interbody fusion (ALIF) procedures. The assembly of FIG. 4 comprises the assembly of FIG. 1 and an insertion instrument 110. The insertion instrument 110 will now be described with reference to FIG. 5.

Figure 5:
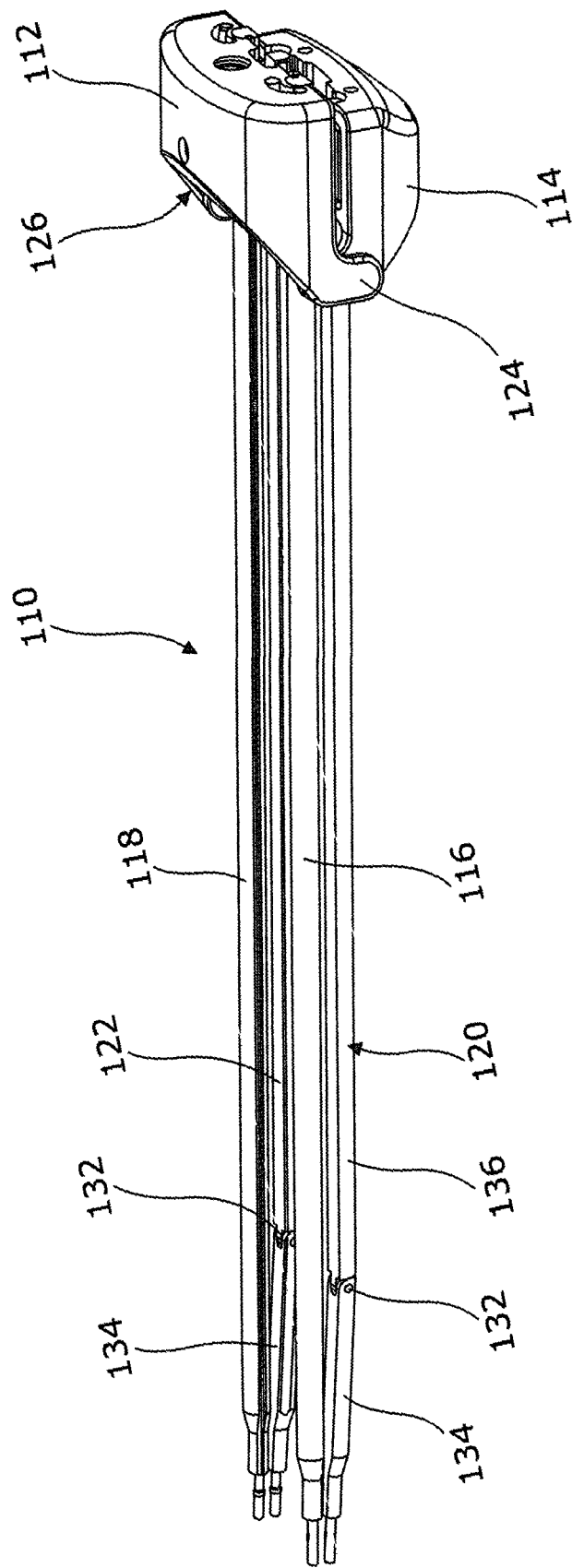
FIG. 5 is a perspective view of the insertion instrument of the second embodiment shown in FIG. 4.

The insertion instrument 110 of FIG. 5 comprises a superior support 112, an inferior support 114, a pair of superior arms consisting of a first superior arm 116 and a second superior arm 118, and a pair of inferior arms consisting of a first inferior arm 120 and a second inferior arm 122. The pair of superior arms 116, 118 are mounted on the superior support 112 such that they extend from spaced apart locations on the superior support and such that the superior arms are substantially parallel. The pair of inferior arms 120, 122 are mounted on the inferior support 114 such that they extend from spaced apart locations on the inferior support 114 and such that the inferior arms are substantially parallel. The superior support 112 and the inferior support 114 are mechanically coupled to each other by a first hinge mechanism 124 and a second hinge mechanism 126. The first hinge mechanism 124 is at a first side of the superior and inferior supports 112, 114 and the second hinge mechanism 126 is at a second side of the superior and inferior supports, the first and second sides facing in opposite directions. Each of the first and second hinge mechanisms 124, 126 is constituted by a cylindrical protrusion on the superior support 112 which is received in a slot 146 in the inferior support 114 whereby the protrusion can rotate in the slot and also travel along the slot. The first and second hinge mechanisms 124, 126 allow the superior support 112 and the inferior support 114 to rotate relative to each other and for the superior and inferior supports to be moved together and apart whilst restricting other relative movement of the superior and inferior supports such as in the direction of the arms, or in the direction of separation of the superior arms or of the inferior arms. The superior support 112 and the inferior support 114 thus rotate about a support axis which is substantially orthogonal to a longitudinal axis of the arms 116, 118, 120, 122 and substantially orthogonal to a direction of separation of the superior and inferior supports. Relative rotation of the superior and inferior supports 112, 114 causes the pair of superior arms 116, 118 and the pair of inferior arms 120, 122 to rotate relative each other. Movement of the superior and inferior supports 112, 114 together and apart moves the pair of superior arms 116, 118 and the pair of inferior arms 120, 122 together and apart. The first and second hinge mechanisms 124, 126 allow for relative rotation of superior and inferior supports 112, 114 at the same time as movement of the superior and inferior supports 112, 114 together and apart.

Mechanical coupling of the superior and inferior supports 112, 114 by way of the first and second hinge mechanisms 124, 126 is such that the pair of superior arms 116, 118 and the pair of inferior arms 120, 122 extend generally in the same direction. Although FIG. 5 shows the pair of superior arms 116, 118 as parallel to the pair of inferior arms 120, 122, increased separation of the superior and inferior supports 112, 114 accompanied by relative rotation of the superior and inferior supports causes the pair of superior arms and the pair of inferior arms to be angled to each other. Nevertheless, the pair of superior arms 116, 118 and the pair of inferior arms 120, 122 extend generally in the same direction despite the angulation.

The superior and inferior supports 112, 114 are manipulated by the surgeon to increase their separation and to angle the pair of superior arms 116, 118 and the pair of inferior arms 120, 122 relative to each other. As can be seen from FIG. 5, each of the four arms tapers towards its distal end with a distal portion having the form of a cylinder. Each distal portion is sized and shaped to be a snug fit in a respective bore proved in an endplate 14, 16 of an anterior lumbar interbody fusion (ALIF) device whereby the superior and inferior endplates of the ALIF device are supported by the four arms. The superior and inferior endplates 14, 16 can therefore be manipulated by the surgeon by movement of the superior and inferior supports 112, 114 while the superior and inferior endplates are supported properly by the four arms.

Considering FIG. 5 further, each of the first and second inferior arms 120, 122 has a hinge 132 spaced apart from the distal end of the arm. The hinge 132 allows for a distal portion 134 between the distal end and the hinge and a proximal portion 136 between the hinge and the inferior support 114 to rotate relative to each other. The hinge 132 rotates about a hinge axis which is substantially parallel to the support axis of rotation whereby the distal portion 134 of the first inferior arm 120 rotates towards and away from the first superior arm 116 and the distal portion 134 of the second inferior arm 122 rotates towards and away from the second superior arm 118. In contrast, the first and second superior arms 116, 118 are unarticulated.

Referring again to FIG. 4, the sizing instrument 12 is brought into engagement with the insertion instrument 110. This is done when the sizing instrument 12 and the insertion instrument 110 are outside the body. Alternatively, insertion instrument 110 is used alone to insert the superior and inferior endplates 14, 16 into the intervertebral space with the sizing instrument 12 then being brought into engagement with the insertion instrument 110 and while the superior and inferior endplates are held in the intervertebral space by the insertion instrument. As described above, the elongate support portion 24 defines first and second linear projections 30, 32 which are oppositely directed and which extend along the sides of the elongate support portion 24. The superior support 112 and the first superior arm 116 and a second superior arm 118 define first and second recesses which extend in the longitudinal direction. The sizing instrument 12 is brought into engagement with the insertion instrument 110 such that the first and second linear projections 30, 32 are received respectively in the first and second recesses defined in the superior support 112. Upon further sliding engagement of the sizing instrument 12 with the insertion instrument 110, the first and second linear projections 30, 32 are received respectively in the first and second recesses defined in the first and second superior arms 116, 118. The first arm 20 of the sizing instrument 12 thus inter-engages with the superior support 112 and with the first and second superior arms 116, 118.

Upon yet further insertion of the sizing instrument 12, the elongate support portion 24 of the first arm 20 inter-engages with the superior endplate 14 as described above with reference to the first embodiment. The third member assembly of the present embodiment is constituted differently from the third member assembly 40 of the first embodiment as will now be described. The third member assembly of the present embodiment lacks the elongate transversely extending protrusion 54 and the first and second protrusions 60, 62 whereby the third member assembly of the present embodiment does not inter-engage with the inferior endplate 16. Instead, the inferior endplate 16 is supported by the insertion instrument 110 and the third member assembly merely engages with the inferior endplate by pushing against the inferior endplate. Pushing against the inferior endplate moves the inferior endplate 16 relative to the superior endplate 14 to change the height and angle. Otherwise, the sizing trial is carried out as described above with reference to the first embodiment. When the sizing trial is complete, the sizing instrument 12 is withdrawn from the intervertebral space while the insertion instrument 110 continues to hold the superior and inferior endplates 14, 16 in the intervertebral space. A core of corresponding height and angle is then selected and inserted into the intervertebral space between the superior and inferior endplates 14, 16 held there by the insertion instrument 110. The core is inserted by means of the core inserter described below.

Figure 6:
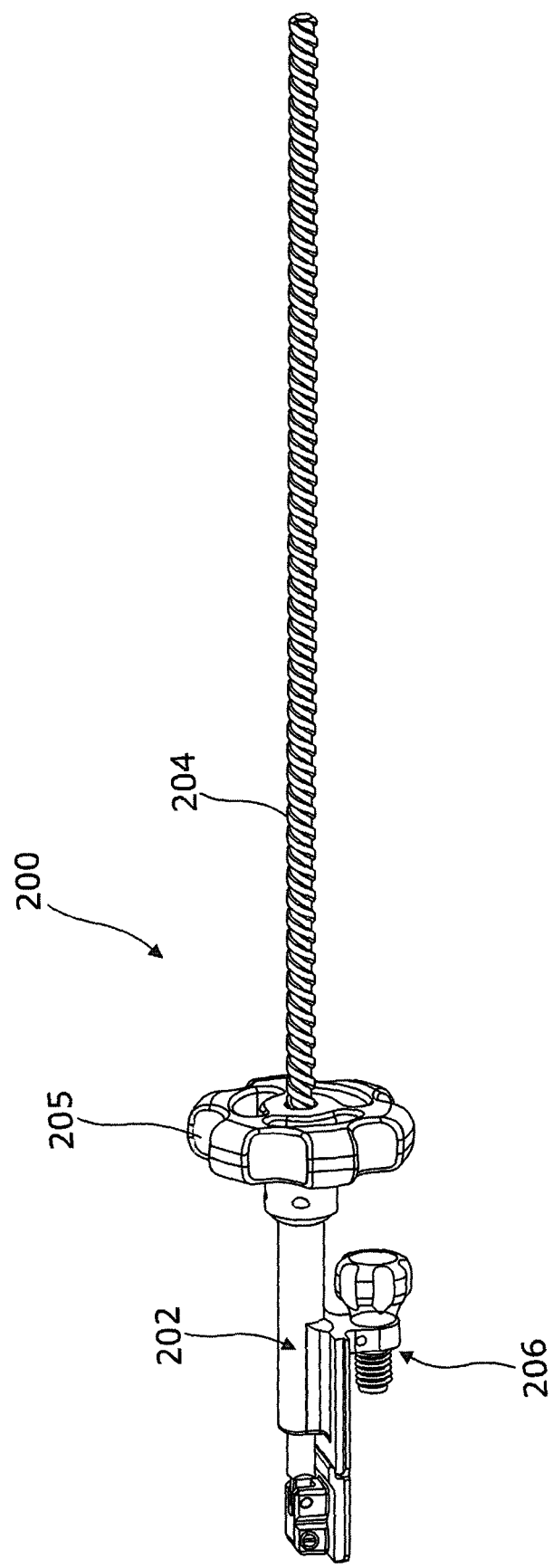
FIG. 6 is a perspective view of a core inserter used with the second embodiment shown in FIG. 4.

A perspective view of a core inserter 200 is shown in FIG. 6. The core inserter is used with the second embodiment of FIGS. 4 and 5. The core inserter 200 comprises a core inserter support 202 and an elongate cylindrical member 204. A core inserter knob 205 is rotatably mounted on the core inserter support 202. The elongate cylindrical member 204 threadedly engages with the core inserter knob 205 whereby the cylindrical member moves through the core inserter support upon rotation of the core inserter knob 205 on the core inserter support. The core inserter support 202 comprises an attachment mechanism 206 which enables the core inserter support to be removably and threadedly attached to the superior or inferior support 112, 114 of the insertion instrument 110 and such that the cylindrical member 204 is directed between the pair of superior arms 116, 118 and the pair of inferior arms 120, 122 of the insertion instrument 110. The surgeon rotates the core inserter knob 205 to move the cylindrical member 204 through the core inserter support 202 to increase the extent to which the cylindrical member is received between the pair of superior arms and the pair of inferior arms of the insertion instrument 110. The operative end of the cylindrical member 204 (i.e. the end of the cylindrical member received between the pair of superior arms and the pair of inferior arms) bears against the selected core to thereby push the selected core towards and then in between the superior and inferior endplates 14, 16 held by the insertion instrument 110.

The invention claimed is:

1. An assembly for determining height and angle of an intervertebral device to be implanted in an intervertebral space, the assembly comprising:
an intervertebral device comprising a superior endplate and an inferior endplate; and
a sizing instrument comprising a support attached to first and second arms which extend in generally a same direction from the support;
one of the superior endplate and the inferior endplate of the intervertebral device engaging with a distal end of the first arm, and the other of the superior endplate and the inferior endplate of the intervertebral device engaging with a distal end of the second arm, the superior and inferior endplates opposing each other when they are engaged with the respective arms, wherein the distal end of the second arm performs first and second forms of movement relative to the distal end of the first arm, the first and second forms of movement being independent of each other, the distal end of the second arm moving along different respective paths in the first and second forms of movement, the first form of movement changing separation between the superior and inferior endplates, the second form of movement changing an angle between the superior and inferior endplates, and wherein the support comprises a user control which is mechanically coupled to at least the second arm of the first and second arms to provide upon user operation of the user control each of the first and second forms of movement of the distal end of the second arm.

2. The assembly according to claim 1, wherein the first arm is constituted such that the distal end engaging with the one of the superior and inferior endplates is immovable relative to the support whereby the respective engaged endplate does not move relative to the support.

3. The assembly according to claim 2, wherein the first arm comprises an elongate first unitary member which extends from the support, a distal end of the first unitary member constituting the distal end of the first arm.

4. The assembly according to claim 3, wherein the distal end of the first unitary member comprises at least one formation which is received in and moves along a respective keyway defined by the respective engaged endplate.

5. The assembly according to claim 1, wherein the second arm is mounted towards its proximal end for rotation relative to the support to thereby provide the first form of movement, the second arm rotating about an axis which is substantially orthogonal to a longitudinal direction of the second arm and substantially orthogonal to a direction of separation of the first and second arms.

6. The assembly according to claim 5, wherein the second arm comprises a second unitary member, which is rotatably coupled towards its proximal end to the first arm such that the second unitary member extends from the support, and a member assembly, which is rotatably coupled at its proximal end to a distal end of the second unitary member, the member assembly rotating relative to the second unitary member about an axis which is substantially parallel to an axis of rotation of the second unitary member relative to the first arm.

7. The assembly according to claim 6, wherein the distal end of the first arm and the member assembly are mechanically coupled to each other to allow for movement together and apart of the distal end of the first arm and the member assembly while resisting change in angle between the distal end of the first arm and the member assembly.

8. The assembly according to claim 7, wherein the distal end of the first arm and the member assembly are mechanically coupled to each other by an extension mechanism which allows substantially only one degree of freedom of movement of the distal end of the first arm and the member assembly relative to each other.

9. The assembly according to claim 8, wherein the distal end of the first arm and the member assembly are mechanically coupled to each other by a scissors mechanism operative to change a separation between first and second ends of the scissors mechanism, the first end of the scissors mechanism mechanically coupled to the distal end of the first arm and the second, opposite end of the scissors mechanism mechanically coupled to the member assembly.

10. The assembly according to claim 8, wherein the first arm comprises an elongate support portion and an elongate movable portion, the elongate support portion immovably attached at its proximal end to the support and engaging with the respective engaged endplate at its distal end, wherein the elongate movable portion is mounted for movement relative to the elongate support portion in a longitudinal direction of the first arm, and wherein an end of the elongate movable portion is mechanically coupled to the extension mechanism to provide for extension and contraction of the extension mechanism.

11. The assembly according to claim 10, wherein the elongate movable portion is mechanically coupled to the user control whereby user operation of a height adjustment control in the user control causes movement of the elongate movable portion.

12. The assembly according to claim 11, wherein the height adjustment control comprises a control knob and a threaded shaft which threadedly engages with the control knob, rotation of the control knob causing linear movement of the threaded shaft in the longitudinal direction of the first arm, and wherein the threaded shaft is mechanically coupled to the elongate movable portion whereby the threaded shaft pushes the elongate movable portion away from the support when the control knob is turned in a first direction and pulls the elongate movable portion towards the support when the control knob is turned in a second, opposite direction.

13. The assembly according to claim 1, wherein, to provide the second form of movement, the distal end of the second arm comprises a tilting member which is mounted for changing an extent of protrusion of the tilting member from a surface of the distal end of the second arm facing the endplate engaged with the first arm, and wherein the second arm is mounted for movement relative to the support in a longitudinal direction of the second arm, longitudinal movement of the second arm changing an extent of protrusion of the tilting member, the tilting member bearing against the endplate engaged with the second arm to thereby tilt the endplate.

14. The assembly according to claim 13, wherein the second arm comprises a second unitary member and a member assembly, the member assembly comprises a first distal part and a second distal part, and the first distal part rotatably coupled at its proximal end to the distal end of the second unitary member, and wherein the second distal part engages with the respective engaged endplate and the tilting member is mounted on the second distal part for rotation relative to the second distal part, rotation of the tilting member changing an extent to which an end of the tilting member protrudes from the second distal part.

15. The assembly according to claim 14, wherein the first distal part is mechanically coupled to the tilting member, and the first distal part moves relative to the second distal part in the longitudinal direction of the second arm, longitudinal movement of the second unitary member causing longitudinal movement of the first distal part relative to the second distal part to thereby rotate the tilting member.

16. The assembly according to claim 13, wherein the user control comprises a trigger mechanism which is mechanically coupled to the second arm to cause longitudinal movement of the second arm upon operation of the trigger mechanism.

17. The assembly according to claim 1 further comprising plural cores of differing heights and angles from which a selection is made upon completion of at least one sizing trial comprising determining height and angle of the intervertebral device to be implanted.

18. The assembly according to claim 1 further comprising an insertion instrument.

* * * * *